United States Patent
Frantz

(10) Patent No.: US 8,952,052 B2
(45) Date of Patent: Feb. 10, 2015

(54) USE OF LIPOIC ACID FOR TREATING OR PREVENTING DEGENERATIVE JOINT CONDITIONS, OSTEOARTHRITIS, CARTILAGE DAMAGE, AND RELATED DISORDERS IN COMPANION ANIMALS

(75) Inventor: Nolan Zebulon Frantz, Meadville, PA (US)

(73) Assignee: Hill's Pet Nutrition, Inc., Topeka, KS (US)

(*) Notice: Subject to any disclaimer, the term of this patent is extended or adjusted under 35 U.S.C. 154(b) by 48 days.

(21) Appl. No.: 13/142,913

(22) PCT Filed: Dec. 29, 2009

(86) PCT No.: PCT/US2009/069684
§ 371 (c)(1),
(2), (4) Date: Jun. 30, 2011

(87) PCT Pub. No.: WO2010/078322
PCT Pub. Date: Jul. 8, 2010

(65) Prior Publication Data
US 2011/0269827 A1    Nov. 3, 2011

Related U.S. Application Data

(60) Provisional application No. 61/141,320, filed on Dec. 30, 2008.

(51) Int. Cl.
*A61K 31/385* (2006.01)
*A61P 19/04* (2006.01)
*A61P 19/00* (2006.01)
*A61P 19/02* (2006.01)
*A23K 1/16* (2006.01)
*A23K 1/18* (2006.01)

(52) U.S. Cl.
CPC ............. *A61K 31/385* (2013.01); *A23K 1/1618* (2013.01); *A23K 1/1846* (2013.01); *A23K 1/1866* (2013.01)
USPC ......................................................... 514/440

(58) Field of Classification Search
USPC ......................................................... 514/440
See application file for complete search history.

(56) References Cited

U.S. PATENT DOCUMENTS

| | | | |
|---|---|---|---|
| 3,997,675 A | 12/1976 | Eichelburg |
| 5,292,538 A | 3/1994 | Paul et al. |
| 5,339,771 A | 8/1994 | Axelrod |
| 5,419,283 A | 5/1995 | Leo |
| 5,569,670 A | 10/1996 | Weischer et al. |
| 5,595,729 A | 1/1997 | Barr et al. |
| 5,621,117 A | 4/1997 | Bethge et al. |
| 5,916,912 A | 6/1999 | Ames et al. |
| 6,042,816 A | 3/2000 | Shen et al. |
| 6,228,418 B1 | 5/2001 | Gluck et al. |
| 6,379,727 B1 | 4/2002 | Addy |
| 6,482,856 B1 | 11/2002 | Katz |
| 6,914,071 B2 | 7/2005 | Zicker et al. |
| 6,943,190 B2 | 9/2005 | Fink et al. |
| 8,168,161 B2 | 5/2012 | Scherl et al. |
| 8,226,973 B2 | 7/2012 | Pan |
| 8,592,478 B2 | 11/2013 | Zicker et al. |
| 8,669,282 B2 | 3/2014 | Zicker et al. |
| 8,722,112 B2 | 5/2014 | Zicker et al. |
| 2001/0043983 A1 | 11/2001 | Hamilton |
| 2002/0006907 A1 | 1/2002 | Gardiner et al. |
| 2002/0025310 A1 | 2/2002 | Bland |
| 2002/0076469 A1 | 6/2002 | Zicker et al. |
| 2002/0076470 A1 | 6/2002 | Zicker et al. |
| 2003/0190343 A1 | 10/2003 | Thombre et al. |
| 2003/0224061 A1 | 12/2003 | Pacioretty et al. |
| 2004/0198998 A1 | 10/2004 | Holerca et al. |
| 2004/0228887 A1 | 11/2004 | Champ et al. |
| 2004/0265255 A1 | 12/2004 | Holerca et al. |
| 2005/0036967 A1 | 2/2005 | Allen et al. |
| 2005/0085454 A1 | 4/2005 | Ghosal |
| 2005/0123628 A1 | 6/2005 | Zabrecky |
| 2005/0192352 A1 | 9/2005 | Caterson et al. |
| 2005/0222050 A1 | 10/2005 | Pan |
| 2005/0232976 A1 | 10/2005 | Zicker et al. |
| 2006/0134014 A1 | 6/2006 | Scherl et al. |
| 2006/0153964 A1 | 7/2006 | Repo |
| 2006/0228448 A1 | 10/2006 | Boileau et al. |
| 2006/0263344 A1 | 11/2006 | Skop et al. |

(Continued)

FOREIGN PATENT DOCUMENTS

| CN | 1578627 | 2/2005 |
|---|---|---|
| DE | 19818563 | 10/1999 |

(Continued)

OTHER PUBLICATIONS

Aafco, 2003, Official Publication of the American Association of Feed Control Officials, p. 220.
Aafco, 2004, American Association of Feed Control Officials Official Publication pp. 129-137.
Amudha et al., 2007, "Protective effect of lipoic acid on oxidative and peroxidative damage in cyclosporine A-induced renal toxicity," Int'l Immunopharmacology, 7(11):1442-1449.
"Dysgeusia" Encyclopedia article, downloaded from www.absoluteastronomy.com/topics/Dysgeusia, dated Sep. 7, 2008, 5 pages.
German, 2006, "The growing problem of obesity in dogs and cats," Nutr., 136(7):1940S-1946S.

(Continued)

*Primary Examiner* — San-Ming Hui
*Assistant Examiner* — Kathrien Cruz
(74) *Attorney, Agent, or Firm* — Thomas M. Hunter

(57) ABSTRACT

The invention encompasses pet food compositions and uses thereof for the treatment and/or prevention of diseases or disorders in companion animals, for example, for the treatment or prevention of degenerative joint conditions, osteoarthritis, cartilage damage, and maintaining or increasing bone mineral density, wherein the compositions and uses include feeding a companion animal a composition including uses acid or a salt thereof.

23 Claims, No Drawings

(56) References Cited

U.S. PATENT DOCUMENTS

| | | |
|---|---|---|
| 2006/0270625 A1 | 11/2006 | Vinik et al. |
| 2007/0231371 A1 | 10/2007 | Pan et al. |
| 2007/0264287 A1 | 11/2007 | Zicker et al. |
| 2008/0038323 A1 | 2/2008 | Zicker et al. |
| 2008/0233244 A1 | 9/2008 | Swenson |
| 2008/0299286 A1 | 12/2008 | Josephson et al. |
| 2009/0149529 A1 | 6/2009 | Zicker et al. |
| 2009/0156658 A1 | 6/2009 | Zicker et al. |
| 2009/0182032 A1 | 7/2009 | Zicker et al. |
| 2010/0056633 A1 | 3/2010 | Gastner |

FOREIGN PATENT DOCUMENTS

| | | |
|---|---|---|
| EP | 1118332 | 7/2001 |
| EP | 1247456 | 10/2002 |
| JP | 2006-219467 | 8/2006 |
| JP | 2007-308468 | 11/2007 |
| JP | 2008-280322 | 11/2008 |
| WO | WO 01/58271 | 8/2001 |
| WO | WO 2004/093995 | 11/2004 |
| WO | WO 2004/112776 | 12/2004 |
| WO | WO 2005/000331 | 1/2005 |
| WO | WO 2005/041999 | 5/2005 |
| WO | WO 2006/042728 | 4/2006 |
| WO | WO 2006/053010 | 5/2006 |
| WO | WO 2006/058248 | 6/2006 |
| WO | WO 2006/074089 | 7/2006 |
| WO | WO 2006/122196 | 11/2006 |
| WO | WO 2007/022344 | 2/2007 |
| WO | WO 2007/063095 | 6/2007 |
| WO | WO 2008/052712 | 5/2008 |

OTHER PUBLICATIONS

Lexis et al., 2006, "Alpha-tocopherol and alpha-lipoic acid enhance the erythrocyte antioxidant defence in cyclosporine A-treated rats," Basic & Clinical Pharmacology & Toxicology, 98(1):68-73.
Loftin et al., 2009, "Therapy and outcome of suspected alpha lipoic acid toxicity in two dogs," J. Vet. Emergency and Critical Care, 19(5):501-506.
Welge-Lussen, Review Article, "Re-establishment of olfactory and taste functions," downloaded from www.egms.de/en/journals/cto/2005-4/cto000012.shtml., dated Sep. 28, 2005.
International Search Report issued for International Application No. PCT/US2009/069684, mailed Apr. 8, 2010.
International Search Report issued for International Application No. PCT/US2009/069679, mailed Apr. 7, 2010.
International Search Report issued for International Application No. PCT/US2009/069665, mailed May 27, 2010.
International Search Report issued for International Application No. PCT/US2009/069654, mailed May 12, 2010.
Jensen, 2003, "Lipoic Acid Helps Restore Smell and Taste," Life Enhancement Magazine, downloaded from http://www.life-enhancement.com/magazine/May/2003 (Copyrighted 2013).
Markova et al., "Pharmacology," 2nd Edition, Saint Petersburg, 2001.
Drinda et al., 1999, "Antioxidant properties of lipoic acid in vegetable oils and lard," Z. Lebensm Unters Forsch A 208:270-276.
Kim et al., 2006, "Antioxidant α-lipoic acid inhibits osteoclast differentiation by reducing nuclear factor-κB DNA binding and prevents in vivo bone resporoion induced by receptor activator of nuclear factor-κB ligand and tumor necrosis factor-α," Free Radical Biology & Medicine 40:1483-1493.
Kim et al., 2006, "Composition for preventing and treating osteoporosis comprising alpha-lipoic acid or dihydrolipoic acid," Database WPI/Thomson AN: 2006-517776 & KR 2005-0051054, Abstract.
Lee et al., 2010, "Homocysteine-lowering therapy or antioxidant therapy for bone loss in Parkinson's Disease," Movement Disorders 25(3):332-340.
Mainini et al., 2012, "Oral supplementation with antioxidant agents containing alpha lipoic acid: effects on postmenopausal bone mass," Clin. Exp. Obstetrics Gynecology 39(4):489-493.
Navari-Izzo et al., 2002 "Lipoic Acid: A unique antioxidant in the detoxification of activated oxygen species," Plant Physiol. Biochem. 40:463-470.
International Search Report and Written Opinion issued for International Application No. PCT/US2009/069654, mailed May 12, 2010.
"Palatability—More Than a Matter of Taste," Behavioral Principles & Practices—Feedback, No. 1.3.1; downloaded from http://www.extension.usa.edu/files/publications/factsheet/I.3_1.pdf, dated Mar. 1, 2003, 3 pages.
Wortinger, 2005, "Nutritional Myths," J. Anim. Hosp. Assoc. 41:273-276.
Yeomans, 1998, "Taste, palatability and the control of appetite," Proc. Nutr. Soc. 57:609-615.
Kiebzak GM1, Learny LJ, Pierson LM, Nord RH, Zhang, Measurement precision of body composition variables using the lunarDPX-L densitometer, J. Clin. Densitom, 2000 Spring:3(1):35-41 (abstract only).
Vitamin E Fact Sheet for Health Professionals, downloaded from http://ods.od.nih.gov/factsheets/VitaminE-HealthProfessional, 9 pages, dated Jun. 2011.

USE OF LIPOIC ACID FOR TREATING OR PREVENTING DEGENERATIVE JOINT CONDITIONS, OSTEOARTHRITIS, CARTILAGE DAMAGE, AND RELATED DISORDERS IN COMPANION ANIMALS

CROSS-REFERENCE TO RELATED APPLICATIONS

This application is a national stage entry under 35U.S.C. §371 of International Patent Application No. PCT/US2009/0069684, filed 29 Dec. 2009 , which claims priority to U.S. Provisional Patent Application No. 61/141,320, which was filed 30 Dec. 2008, which is incorporated herein by reference in its entirety.

FIELD OF THE INVENTION

The invention encompasses methods for the treatment and/or prevention of diseases or disorders in companion animals, for example, for the treatment or prevention of degenerative joint conditions, osteoarthritis, cartilage damage, and maintaining or increasing bone mineral density, wherein the compositions and methods include feeding a companion animal a composition including lipoic acid or a salt thereof.

BACKGROUND OF THE INVENTION

Virtually all joints have cartilage. Cartilage is important in the body of animals for providing flexibility, compressibility under pressure, cushion, tensile strength, range of motion and smoothness of movement within joints. Examples of joints having cartilage include fingers and toes, neck, knee, hip, shoulder and the like. Animals can suffer from a number of conditions where cartilage is negatively affected thereby bringing about a reduction in the joint's flexibility, compressibility and often times resulting in a generalized inflammation of the joint and/or tissue surrounding the joints. Such animals then have significant loss of joint function and experience pain.

Large dogs may develop arthritis as they age. Large dog breeds are more susceptible to arthritis due to their increased mass and/or genetic disposition. Large dogs are not the only animals at risk of arthritis and other cartilage conditions. Arthritis and other degenerative joint diseases have been commonly recognized in dogs and such conditions have been shown to be prevalent in cats. Animals at risk of developing cartilage-affecting conditions include, but are not limited to, mammals such as canine, feline, equine, hircine, ovine, porcine, bovine, human and non-human primate species, and birds including turkeys and chickens.

An important indicator of animal health is the body composition of the animal. An unhealthy diet and/or an unhealthy lifestyle can result in the animal having an unhealthy proportion of body fat, particularly in relation to lean muscle in the body. It is thought that a body fat amount in excess of 30% by weight indicates that the animal is unhealthy, particularly if the amount of body fat is in excess of 35% by weight.

The invention encompasses pet food compositions for companion animals, which have increased therapeutic and prophylactic efficacy over currently marketed companion food products.

SUMMARY OF THE INVENTION

The inventors have developed rood compositions and methods of using compositions for treating or preventing disorders in animals.

The invention encompasses a companion pet diet meeting ordinary nutritional requirements of a companion pet and further comprising an effective amount of one or more antioxidants, for example, lipoic acid.

Another embodiment encompasses methods for treating or preventing a degenerative joint condition in a companion animal, which includes feeding the companion animal a food composition including lipoic acid or a salt thereof in an amount effective to treat or prevent the degenerative joint condition.

Another embodiment encompasses methods for treating or preventing osteoarthritis in a companion animal, which includes feeding the animal a composition including lipoic acid or a salt thereof in an amount effective to treat or prevent osteoarthritis.

Another embodiment encompasses methods for treating or preventing cartilage damage in a companion animal, which includes feeding the animal a composition including lipoic acid or a salt thereof in an amount effective to treat or prevent cartilage damage.

Another embodiment encompasses methods for modulating enzymatic degradation of articular cartilage in a companion animal, which includes feeding the animal a composition including lipoic acid or a salt thereof in an amount effective to modulate the enzymatic degradation of the articular cartilage.

Another embodiment encompasses methods for decreasing: release of glycosaminogiycan ("GAG") from cartilage tissue of a companion animal, which includes feeding the animal a composition including lipoic acid or a salt thereof in an amount effective to decrease GAG release from the cartilage tissue.

Another embodiment encompasses methods for maintaining or increasing hone mineral density and mineral content in a companion animal including feeding the animal a composition including lipoic acid or a salt thereof in an amount effective to maintain or increase bone mineral density.

DETAILED DESCRIPTION OF THE INVENTION

General Description

The invention encompasses food compositions including an effective amount of lipoic acid or a salt thereof to prevent or treat disorders in a companion animal in need thereof.

One embodiment encompasses a method for treating or preventing osteoarthritis in a companion animal, which comprises feeding the animal a composition comprising lipoic acid or a salt thereof in an amount effective to treat or prevent osteoarthritis.

In certain embodiments, the effective amount is at least about 25 ppm.

In certain embodiments, the effective amount is at least about 50 ppm.

In certain embodiments, the effective amount is a least about 100 ppm.

In certain embodiments, the effective amount is about 100 ppm to about 600 ppm.

In certain embodiments, the effective amount is about 100 ppm to about 200 ppm.

In certain embodiments, the companion animal is a dog.

In certain embodiments, the companion animal is a cat.

In certain embodiments, the composition further comprises a protein, fat, carbohydrate, fiber, and combinations thereof.

In certain embodiments, the composition is a dog food.

In certain embodiments, the composition is a cat food.

In certain embodiments, the composition is a food, a nutritional diet, a supplement, an animal treat, or a toy.

In certain embodiments, the composition is in the form of a moist food.

In certain embodiments, the composition is in the form of a dry food.

Another embodiment encompasses a method for modulating enzymatic degradation of articular cartilage in a companion animal, which comprises feeding the animal a composition comprising lipoic acid or a salt thereof in an amount effective to modulate the enzymatic degradation of the articular cartilage.

In certain embodiments, the effective amount of lipoic acid is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the composition further comprises a protein, fat, carbohydrate, fiber, and combinations thereof.

In certain embodiments, the composition is a dog food.

In certain embodiments, the composition is a cat food.

In certain embodiments, the composition is a food, a nutritional diet, a supplement, an animal treat, or a toy.

In certain embodiments, the composition is in the form of a moist food.

In certain embodiments, the composition is in the form of a dry food.

In certain embodiments, the companion animal is a dog.

In certain embodiments, the companion animal is a cat.

Another embodiment of the invention encompasses methods for treating or preventing a degenerative joint condition in a companion animal, which includes feeding the animal a composition of the invention, which includes lipoic acid or a salt thereof in an amount effective to treat or prevent the degenerative joint condition. In one embodiment, the degenerative joint condition is osteoarthritis or cartilage damage.

In certain embodiments, the effective amount of lipoic acid is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the composition further comprises a protein, fat, carbohydrate, fiber, and combinations thereof.

In certain embodiments, the composition is a dog food.

In certain embodiments, the composition is a cat food.

In certain embodiments, the composition is a food, a nutritional diet, a supplement, an animal treat, or a toy.

In certain embodiments, the composition is in the form of a moist food.

In certain embodiments, the composition is in the form of a dry food.

In certain embodiments, the companion animal is a dog.

In certain embodiments, the companion animal is a cat.

Another embodiment of the invention encompasses methods for decreasing release of GAG from cartilage tissue of a companion animal, which included feeding the animal a composition of the invention, which includes lipoic acid or a salt thereof in an amount effective to decrease GAG release from the cartilage tissue.

In certain embodiments, the effective amount of lipoic acid is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the composition further comprises a protein, fat, carbohydrate, fiber, and combinations thereof In certain embodiments, the composition is a dog food.

In certain embodiments, the composition is a cat food.

In certain embodiments, the composition is a food, a nutritional diet, a supplement, an animal treat, or a toy.

In certain embodiments, the composition is in the form of a moist food.

In certain embodiments, the composition is in the form of a dry food.

In certain embodiments, the companion animal is a dog.

In certain embodiments, the companion animal is a cat.

Another embodiment of the invention encompasses methods for maintaining or increasing bone mineral density in a companion animal including feeding the animal a composition of the invention, which includes lipoic acid or a salt thereof in an amount effective to maintain or increase bone mineral density.

In certain embodiments, the effective amount of lipoic acid is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the composition further comprises a protein, fat, carbohydrate, fiber, and combinations thereof.

In certain embodiments, the composition is a dog food.

In certain embodiments, the composition is a cat food.

In certain embodiments, the composition is a food, a nutritional diet, a supplement, an animal treat, or a toy.

In certain embodiments, the composition is in the form of a moist food.

In certain embodiments, the composition is in the form of a dry food.

In certain embodiments, the companion animal is a dog.

In certain embodiments, the companion animal is a cat.

The term "companion animal" used in the present invention includes any non-human animal suitable for being kept as a pet by humans including a dog, a cat, and a rodent. All aspects of the present invention are preferably for the treatment of cats and/or dogs.

The term "dog" includes those dogs, which are companion animals such as *Canis familiaris*, working dogs and the like. The term dog is synonymous with the term canine.

The term "cat" includes those cats, which are, companion animals known as domestic cats or house cats.

The term "rodent" includes, but is not limited to hamsters, mice, rats, guinea pigs, gerbils, rabbits, hedge hogs, ferrets, chinchillas etc.

All percentages expressed herein are by weight of the composition on dry matter basis unless specifically stated otherwise.

Compositions of the Invention

One embodiment of the invention encompasses compositions for companion animals including an effective amount of lipoic acid to prevent or treat a degenerative joint condition in a companion animal.

As used herein, the terms "lipoic acid or a salt thereof" includes, but is not limited to, for example, alpha-lipoic acid, a racemic mixture of lipoic acids, a lipoate salt, ester, amide or derivative thereof, for example as described in U.S. Pat. No. 5,621,117. In various embodiments, the lipoic acid can be administered in a composition comprising a wet or dry food composition, which may be in the form of a moist food, dry food, supplement or treat. The lipoic acid may be incorporated therein or on the surface of any food composition, such as, by spraying or precipitation thereon or may be added to the diet by way of snack, supplement, treat or in the liquid portion of the diet such as water or another fluid. The lipoic acid may be administered as a powder, solid or as a liquid including a gel. An important aspect is that the animal be provided an effective amount of the lipoic acid to provide a positive effect. Typically, the source of lipoic acid is present in the composition in an amount of up to an amount, which remains nontoxic to the animal.

The quantity of alpha-lipoic acid can vary from at least about 25 ppm, about 50 ppm, about 100 ppm, about 200 ppm, about 300 ppm, about 500 ppm, about 700 ppm, about 900 ppm, about 1100 ppm, about 1200 ppm, about 1400 ppm, about 1600 ppm, about 1800 ppm, about 2000 ppm, about 2200 ppm, about 2400 ppm, about 2600 ppm, about 2800 ppm, about 3000 ppm, or about 3500 ppm. In various embodiments, the range of lipoic acid that can be administered to dogs is about 150 ppm to about 4500 ppm. In various embodiments, the range of lipoic acid that can be administered to cats is about 65 ppm to about 2600 ppm. In certain illustrative embodiments, quantities can vary from about 100 ppm to an amount which remains nontoxic to the pct, in other embodiments, a range is from about 100 ppm to about 200 ppm.

In various embodiments, a food composition comprising lipoic acid provides a substantially nutritionally complete diet for the intended recipient animal. A "nutritionally complete diet" is a diet that includes sufficient nutrients for maintenance of normal health of a healthy animal on the diet.

The compositions of the invention include lipoic acid or salt thereof in an amount effective to treat or prevent a degenerative joint condition.

The lipoic acid or salt thereof is present at a concentration that is not deleterious to the intended animal's health. Thus, for example, the lipoic acid or salt thereof is present at a concentration that does not cause undesirable or toxic effects.

The composition can be a liquid or a solid food. When the composition is a liquid, the lipoic acid or salt thereof can be admixed with other components. Where the composition is a solid, the lipoic acid may be coated on the composition, incorporated into the composition, or both.

In various embodiments, the lipoic acid or salt thereof may be added to the animal's food. In various embodiments, the lipoic acid or salt thereof may be added to the animal's food by a compounder or manufacturer at a site or by an animal's caregiver prior to feeding the animal. In various embodiments, the lipoic acid or salt thereof may be added during the processing of an animal's food, such as during and/or after mixing of other components of the composition that is then packaged and made available to consumers. Such processing may include extrusion, canning, baking, and the like or any other method or process of producing pet foods that is known in the art. In various embodiments, the lipoic acid or salt thereof may be contributed by a natural source like an animal or plant component, or the lipoic acid or salt thereof may be contributed by a synthetically derived source, or the lipoic acid or salt thereof may be contributed by a mixture of natural and synthetic sources.

The compositions in addition to lipoic acid or a salt thereof include at least one component suitable for consumption by a companion animal including, but not limited to, fats, carbohydrates, proteins, fibers, nutritional balancing agents such as vitamins, minerals, and trace elements, and mixtures thereof. One of ordinary skill in the art can select the amount and type of food ingredients for a typical food based upon the dietary requirements of the animal, for example, the animal's species, age, size, weight, health, and function.

The food ingredient part of the food composition can include up to about 100% of any particular food ingredient or can include a mixture of food ingredients in various proportions. In certain embodiments, the food composition includes a combination of food ingredients in amounts of about 0 wt. % to about 50 wt. % fat, about 0 wt. % to about 75 wt. % carbohydrate, about 0 wt. % to about 95 wt. % protein, about 0 wt. % to about 40 wt. % dietary fiber, and about 0 wt. % to about 15 wt, % of one or more nutritional balancing agents.

In certain embodiments, the fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

In certain embodiments, the protein food ingredient is obtained from a variety sources such as plants, animals, or both. Animal protein includes meat, meat by-products, dairy, and eggs. Meats include the flesh from poultry, fish, and animals such as cattle, swine, sheep, goats, and the like, meat by-products include lungs, kidneys, brain, livers, stomachs, and intestines. The protein food ingredient may also be free amino acids and/or peptides. Preferably, the protein food ingredient includes meat, a meat by-product, dairy products, or eggs.

In certain embodiments, the fiber food ingredient is obtained from a variety of sources such as vegetable fiber sources, for example, cellulose, beet pulp, peanut hulls, and soy fiber.

In certain embodiments, the nutritional balancing agents are obtained from a variety of sources known to skilled artisans, for example, vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press. Wash. D.C., 1998), Nutrient Requirements of Poultry (9th Rev. Ed. Nat'l Academy Press, Wash. D.C., 1994). Nutrient Requirements of Horses (5th Rev. Ed., Nat'l Academy Press. Wash. D.C. 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

In certain embodiments, the food compositions may contain additional ingredients such as vitamins. minerals, fillers, palatability enhancers, binding agents, lavors, stabilizers, etnulsifiers, sweeteners, colorants, buffers, salts, coatings, and the like known to skilled artisans. Stabilizers include substances that tend to increase the shelf life of the composition such as preservatives, synergists and sequestrants, packaging ases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of animal; the animal's age, body weight, general health, sex, and diet; the animal's consumption rate; the type of disease or condition being treated; and the like. Therefore, the component and ingredient amounts may vary widely and may deviate from the preferred proportions described herein.

In one illustrative embodiment, the composition may, for example, in addition to lipoic acid or a salt thereof also include at least one of the following:
  (a) about 0% to about 75% carbohydrate,
  (b) about 2% to about 50% fat,
  (c) about 0% to about 40% dietary fiber, and
  (d) about 0% to about 15% of one or more nutritional balancing agents.

The diet fed to the adult companion pet, for example, canine and feline is the standard normal diet fed to an animal of that age. Below is a typical diet for a canine of 1 to 6 years of age.

TABLE 1

Illustrative Companion Animal Pet Food Composition

| Ingredient | Target |
| --- | --- |
| Protein (% of dry matter) | 23 |
| Fat (% of dry matter) | 15 |
| Phosphorous (% of dry matter) | 0.6 |
| Sodium (% of dry matter) | 0.3 |

The compositions can contain additional ingredients intended to maintain or improve the health of the animal, for example, supplements, medications, herbs, holistic drugs and compositions, and the like.

The composition of the invention may include one or more additional ingredients to prevent or treat one or more diseases or conditions.

The component in the diet which accomplishes this is an antioxidant or mixture thereof. An antioxidant is a material that quenches a free radical. Examples of such materials include foods such as Ginkgo Biloba, citrus pulp, grape pomace, tomato pomace, carrot and spinach, all preferably dried as well as various other materials such as beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, l-carnitine and the like. Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The d form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form such as liquid, semisolid, solid and heat stable form. Alpha-lipoic acid can be administered into the diet as alpha lipoic acid or as a lipoate derivative as in U.S. Pat. No. 5,621,117, racemic mixtures, salts, esters or amides thereof. L-carnitine can be administered in the diet and various derivatives of carnitine such as the salts such as the hydrochloride, fumarate and succinates, as well as acetylated carnitine, and the like can be used.

The quantities administered in the diet, all as wt % (dry matter basis) of the diet, are calculated as the active material, per se, that is measured as free material. The maximum amounts employed should not bring about toxicity. At least about 100 ppm or at least about 150 ppm of Vitamin E can be used. A preferred range of about 500 to about 1,000 ppm can be employed. Although not necessary, a maximum of about 2000 ppm or about 1500 ppm is generally not exceeded. With respect to Vitamin C at least about 50 ppm is used, desirably at least about 75 ppm and more desirably at least about 100 ppm. A non-toxic maximum can be employed. The quantity of alpha-lipoic acid can vary from at least about 25, desirably at least about 50 ppm, more desirably about 100 ppm. Maximum quantities can vary from about 100 ppm to an amount which remains non-toxic to the pet. A preferred range is from about 100 ppm to about 200 ppm. For 1-carnitine about 50 ppm, desirably about 200 ppm, more desirably about 300 ppm for canines are a useful minimum. For felines, slightly higher minimums of l-carnitine can be employed such as about 100 ppm, 200 ppm, and 500 ppm. A non-toxic maximum quantity can be employed, for example, less than about 5,000 ppm. For canines, lower quantities can be employed, for example, less than about 5,000 ppm. For canines, a preferred range is about 200 ppm to about 400 ppm. For felines, a preferred range is about 400 ppm to about 600 ppm. Beta-carotene at about 1-15 ppm can be employed. Selenium at about 0.1 up to about 5 ppm can be employed. Lutein at least about 5 ppm can be employed. Tocotrienols at least about 25 ppm can be employed. Coenzyme Q10 at least about 25 ppm can be employed. S-adenosylmethionine at least about 50 ppm can be employed. Taurine at least about 1000 ppm can be employed. Soy isoflavones at least about 25 ppm can be used. N-acetylcysteine at least about 50 ppm can be used. Glutathione at least about 50 ppm can be used. Gingko Biloba at least 50 ppm of extract can be used.

The following are raw ingredients that are high in ORAC (Oxygen radical absorbing capacity) content: Spinach pomace, Tomato pomace, Citrus Pulp, Grape Pomace, Carrot granules, Broccoli, Green tea, Ginkgo Biloba and Corn gluten meal.

When added to the diet as 1% inclusions (for a total of 5% substitution for a low ORAC ingredient such as corn) they increased the ORAC content of the overall diet and increased the ORAC content of the plasma of the animals which ate the diet containing these components. Preferably, any ingredient with an ORAC content >25 µmole of Trolox equivalents per gram of matter could be used if added at 1% combination with four other 1% ingredients for a total of 5% addition to the diet. In certain embodiments, the compositions further include an effective amount of at least one substance selected from the group consisting of glucosamine, chondroitin, chondroitin sulfate, methylsulfonylmethane ("MSM" creatine, antioxidants, *Perna canaliculata*, omega-3 fatty acids, omega-6 fatty acids and mixtures thereof.

In various embodiments, a supplement including an effective amount of lipoic acid or a salt thereof further includes an effective amount of at least one substance including aspirin, anti-inflammatories such as ibuprofen, COX-2 inhibitors, and other medicinal and pharmaceutical compositions and combinations thereof. Supplements include, but are not limited to, a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Inc. Official Publication, p. 220 (2003). Supplements may be in various forms including, for example, powders, liquids, syrups, pills, and encapsulated compositions.

In certain embodiments, the composition can be a treat. Treats include compositions that are given to an animal to entice the animal to eat during a non-meal time, for example, dog bones for canines. Treats may be nutritional wherein the composition includes one or more nutrients and may have a food-like composition. Non-nutritional treats encompass any other treats that are non-toxic. The composition or components are coated onto the treat, incorporated into the treat, or both. Treats of the invention can be prepared by an extrusion or baking process similar to those used for dry food. Other processes also may be used to either coat the composition on the exterior of existing treat forms or inject the composition into an existing treat form.

In certain embodiments, the composition can be a toy. Toys include chewable toys such as artificial bones. The lipoic acid or a salt thereof can form a coating, on the surface of the toy or on the surface of a component of the toy, be incorporated partially or fully throughout the toy, or both. In one embodiment, the lipoic acid or a salt thereof is orally accessible by the intended user. There are a wide range of suitable toys currently marketed, for example, U.S. Pat. Nos. 5,339,771, 5,419,283, and references disclosed therein. This invention provides both partially consumable toys, for example, toys including plastic components, and fully consumable toys, for example, rawhides and various artificial bones. The invention preferably provides toys for use by a dog or a cat.

Preparation of the Compositions of the Invention

The compositions of the invention may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, for example, direct steam injection or using a vessel fitted with a heat exchanger. Following the addition of the last ingredient, the mixture is heated to a temperature of about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

Food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavours, fats, oils, powders, and the like. Kibble also can be made from the dough using a baking process, rather than extrusion, wherein the dough is placed into a mold before dry-heat processing. The food compositions can be in the form of a treat using an extrusion or baking process similar to those described above for dry food or a toy such as those disclosed in U.S. Pat. Nos. 5,339,771 and 5,419,283. The compositions of the present invention can be added to the food compositions before, during, or after preparation.

Methods of Treating or Preventing Disorders with Compositions of the Invention

The invention also encompasses methods of treating or preventing certain disorders by administering a therapeutically or prophylactically effective amount of a composition including lipoic acid or a salt thereof to a companion animal in need thereof.

The inventors have discovered that the compositions of the invention are useful in treating or preventing a degenerative joint condition in a companion animal. In certain embodiments, the treatment is administered to an adult dog. The term, adult, is intended to mean, in general, a canine of at least 1 to 6 years and a feline of at least 1 to 6 years. An aged dog or cat is 7 years and above.

Accordingly, in another embodiment, the invention encompasses methods of treating or preventing a degenerative joint condition in a companion animal, which includes feeding to the animal a composition of the invention including lipoic acid or a salt thereof in an amount effective to treat or prevent the degenerative joint condition. In certain embodiments of the invention, the composition and method are for the treatment or prevention of a degenerative joint condition in a dog or a cat.

The methods or uses of the compositions of the invention include administering the composition including lipoic acid or a salt thereof to a companion animal susceptible to or suffering from a degenerative joint condition or administering the compositions to an animal experiencing a decline in joint function, particularly a decline due to aging. The composition may also be fed to a healthy companion animal in order to maintain healthy joint functions and/or prevent a degenerative joint condition.

The treatment or prevention of a degenerative joint condition according to the invention includes the treatment or prevention of various cartilage-affected conditions. The invention therefore includes not only treatment of a pre-existing cartilage affecting condition but also for the prevention or protection of animals against a cartilage affecting condition. The invention includes managing a cartilage affecting condition.

The term "managing a cartilage affecting condition" as used herein means to improve, treat, prevent and/or alleviate at least one cartilage-affected condition and/or to provide a positive cartilage effect to an animal. The term "managing a cartilage affecting condition" includes preventative methods for an animal with a latent cartilage effecting condition, a predisposition, whether hereditary or otherwise to a cartilage affected condition or as a preventative measure at any time during an animal's lifetime to strengthen cartilage, prevent abnormalities in cartilage, improve joint health, decrease the effects of joint degradation over age, or to prevent arthritis or other joint affected condition. Illustrative examples of a positive cartilage effect includes increasing flexibility, repairing lesions, reducing inflammation, improving mobility, strengthening cartilage, reducing abnormalities, and/or preventing any of reduced flexibility and/or mobility, weakening and/or degrading cartilage, abnormalities and/or lesions, inflammation, or a cartilage affected condition, and the like. Illustrative examples of such cartilage-affected conditions include osteoarthritis, rheumatoid arthritis, osteochondrosis, degenerative joint disease, synovitis, bacterial purulent arthritis, osteoarthropathia psoriatica and the like.

In another embodiment, the invention encompasses methods for treating or preventing osteoarthritis in companion animals, which includes feeding the animal a composition including lipoic acid or a salt thereof in an amount effective to treat or prevent the osteoarthritis. With respect to prevention of joint damage from osteoarthritis, a particular target group of dogs includes those in need of such preventive care. For example, large breeds such as Labrador retriever, Rottweiler, German shepherd and the like are more susceptible to osteoarthritis as demonstrated by its greater occurrence in these breeds. Additionally, dogs above the age of about 6 years have a significantly greater occurrence of osteoarthritis. Active dogs, athletic dogs and obese dogs can also be at risk.

In another embodiment, the invention encompasses methods for treating or preventing cartilage damage in a companion animal, which includes feeding the animal a composition including a lipoic acid or a salt thereof in an amount effective to treat or prevent the cartilage damage.

In another embodiment, the invention encompasses methods for modulating enzymatic degradation of articular cartilage in a companion animal, which includes feeding the animal a composition including lipoic acid or a salt thereof in an amount effective to modulate the enzymatic degradation of the articular cartilage.

In another embodiment, the invention encompasses methods for decreasing the release of GAG from cartilage tissue of a companion animal including feeding the animal a composition including lipoic acid or a salt thereof in an amount effect to decrease the release of GAG.

Another embodiment of the invention encompasses methods for maintaining or increasing bone mineral density in a companion animal including feeding the animal a composition including lipoic acid or a salt thereof in an amount effective to maintain or increase bone mineral density.

In another aspect, the present invention provides a means for communicating information about or instructions for treating or preventing degenerative joint conditions including managing cartilage affecting conditions, increasing cartilage flexibility, increasing cartilage strength, or preventing cartilage degradation in an animal. The communicating means includes a document, digital storage media, optical storage media, audio presentation, or visual display containing the information or instructions. Preferably, the communication is a displayed web site or a brochure, product label, package insert, advertisement, or visual display containing such information or instructions. Useful information includes one or more of (1) methods and techniques for administering the compositions and using the methods of he ent invention, (2) details about the side effects, if any, caused by using the present invention, alone or in combination with other drugs, and (3 contact information for patients to use if they have a question about the invention and its use. Useful instructions include dosages, administration amounts and frequency, and administration routes. The communication means is useful for instructing on the benefits of using the present invention and communicating the approved methods for using the invention.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "include", "includes", and "including" are to be interpreted inclusively rather than exclusively. Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

Materials and Methods:
Thirty (30) dogs were used to determine the effect of lipoic acid when compared to an AAFCO control food or a test food containing fish oil.

A differential gene expression profile was studied between an AAFCO control food, a food containing fish oil, and a food containing lipoic acid. At a minimum of 1.3 fold change, a list of 1212 genes was generated compared to the AAFCO control and 1896 genes compared to the food containing fish oil at d 30.

RNA extraction: Total RNAs were isolated from whole blood samples using the PAXgene RNA isolation kit. All measurements were done with the canine 2 Affymetrix genechips. For statistical analysis, all measurements were normalized with RMA. All analysis was preformed using Partek. An ANOVA t-test was performed for genes that are differentially expressed between the control and test foods were selected based on p-value cutoff 0.1, fold change >+/−1.3.

Gene Expression: Expression of 1212 genes was found to be altered in dogs fed a test food containing 150 ppm lipoic acid when compared to dogs fed an AAFCO control food. In addition, expression of 1896 genes was found to be altered in dogs fed the test food containing lipoic acid compared to a test food containing fish oil. Table 3 shows the genes grouped by function and the direction of expression relative to those fed either the control food or a food containing fish oil.

Metabolomics: Plasma metabolites were analyzed and were compared as fold change relative to the control fed dogs.

Biomarker measurements: Serum cartilage markers were measured using ELISA based kits to determine concentrations of cartilage markers. Day 0 was used as a covariate in the analysis to adjust for baseline values.

Results: The addition of lipoic acid to a food resulted in a greater decrease in type II collagen C-propeptide and carboxy-terminal crosslinked telopeptide fragment of type II collagen than a similar food without lipoic acid. These two markers are known to increase in dogs with osteoarthritis. Additionally, dogs fed a food containing lipoic acid lost fat suggesting an increase in utilization of fat for energy (fat oxidation) and a decreased production of glucose for healthier weight maintenance, in other words, dogs fed lipoic acid utilized available glucose more efficiently and shifted their metabolism towards mobilization of fat for energy use. Additionally, the metabolite hydroxyproline was reduced in plasma suggesting reduced cartilage destruction as this metabolite almost exclusively originates from cartilage. Furthermore, changes in gene expression as determined from serum white blood cells support the evidence to suggest increased cartilage protection from increased synthesis of cartilage components and decreased expression of enzymes that degrade cartilage. Finally, gene expression changes suggest improved fat utilization by increasing PDK4, which inhibits the formation of pyruvate from glucose and shifts metabolism to shuttling acetyl-CoA for energy, and upregulation of glucose transporters. The dogs fed lipoic acid also appeared genomically leaner compared to dogs led the control food.

The following tables show the difference in fat and weight as well as cartilage markers relative to treatment with lipoic acid.

Table 2 illustrates the change in blood level of arthritic markers in dogs after being fed a control diet compared with dogs fed a control plus fish oil and a control plus lipoic acid for 30 days and measured again at day 90. As illustrated in Table 2, dogs fed a control plus lipoic acid displayed reduction in arthritic markers (i.e., CPII and CTXII) after a 30 day treatment period and a greater reduction in arthritic markers after a 90 day period of being fed a control plus lipoic acid.

TABLE 2

Arthritic markers measured in the blood in dogs fed three different foods[a,b]

| Metabolite | Control | Fish oil | Lipoic acid | SE | Probability, P< Treatment | Fish oil vs Control | Fish oil vs Lipoic acid | Lipoic acid vs Control |
|---|---|---|---|---|---|---|---|---|
| Day 30 | | | | | | | | |
| CPII, ng/mL | 1076.9 | 997.61 | 986.28 | 29.254 | 0.004 | 0.01 | 0.70 | 0.01 |
| Change CPII | 17.00 | −30.50 | −95.10 | 33.863 | 0.01 | 0.17 | 0.07 | 0.01 |
| Change CTXII | −2.33 | −0.03 | −5.60 | 2.622 | 0.12 | 0.39 | 0.04 | 0.22 |
| Day 90 | | | | | | | | |
| CPII, ng/mL | 941.1 | 897.8 | 848.0 | 33.56 | 0.02 | 0.18 | 0.15 | 0.01 |
| Change CPII | −118.70 | −131.00 | −232.70 | 36.546 | 0.01 | 0.74 | 0.01 | 0.01 |
| Change CTXII | −3.24 | −1.23 | −0.59 | 6.119 | 0.90 | 0.75 | 0.92 | 0.67 |

[a]Individual markers analyzed with d 0 as covariate
[b]Change in individual markers and ratios analyzed without covariates.

Table 3 illustrates the directional change (up regulation or down regulation in genes related to cartilage metabolism in dogs after being fed a control diet compared with dogs fed a control plus fish oil and a control plus lipoic acid for 90 days in canine bone cells. As illustrated in Table 2, dogs fed a control plus lipoic acid displayed down regulation in MMP3 gene corresponding to a degradation of the collagen component of cartilage, up-regulation of TIMP2 corresponding to inhibition of MMPs, and up-regulation of prolyl 4-hydroxylase, which corresponds to the rate limiting step in collagen type II synthesis produces hydroxyproline for incorporation into collagen epitope.

TABLE 3

Genes related to cartilage metabolism altered by lipoic acid in canine bone cells

| Gene | Probe | Directional change | Function |
|---|---|---|---|
| MMP3 | 1582602_at | Down | Degradation of collagen component of cartilage |
| TIMP2 | 1582708_at | up | Inhibits MMPs |
| Prolyl 4-hydroxylase | 1600479_at | up | Rate limiting step in collagen type II synthesis, produces hydroxyproline for incorporation into collagen epitope |

Table 4 illustrates the change in genes related to cartilage metabolism and energy metabolism in dogs after being fed a control diet compared with dogs fed a control plus lipoic acid.

TABLE 4

Genes related to cartilage and energy metabolism altered by lipoic acid compared to the control or upgrade foods (upgrade contains fish oil)

| Gene name | Probe | Fold change | lipoic acid vs. |
|---|---|---|---|
| Related to cartilage metabolism | | | |
| Prolyl hydroxylase alpha 1 | CfaAffx.22481.1.S1_at | 1.4 | control |
| Prolyl hydroxylase alpha 2 | Cfa.13303.2.S1_a_at | 1.3 | control |
| Facilitated glucose transporter 9 | Cfa.7132.1.A1_at | 1.4 | control |
| TIMP1 | Cfa.3680.1.S1_s_at | 1.3 | control |
| Chondroitan sulfate synthase 1 | CfaAffx.16537.1.S1_at | 1.4 | control |
| heparin sulfate N-deacetylase/N-sulfotransferase 2 | Cfa.11897.1.A1_at | 1.3 | control |
| 12-lipooxygenase | CfaAffx.25908.1.S1_s_at | −1.3 | control |
| chondroitan sulfate proteoglycan 2 (veriscan) | CfaAffx.13597.1.S1_s_at | 1.5 | control |
| Lysyl hydroxylase | Cfa.16732.1A1_at | 1.3 | fish oil |
| N-acetylgalactosaminyl-transferase 1 | Cfa.12862.1.S1_at | 1.3 | fish oil |
| Chondroitan sulfate synthase 1 | CfaAffx.16537.1.S1_at | 1.3 | fish oil |
| Fibronectin 1 | Cfa.3707.2.S1_at | 1.4 | fish oil |
| chondroitan sulfate proteoglycan 2 (veriscan) | CfaAffx.13597.1.S1_s_at | 1.5 | fish oil |
| ADAMTS-2 | Cfa.6326.1.A1_x_at | −1.3 | fish oil |
| ADAMTS-10 | | −1.3 | fish oil |
| ADAMTS-16 | CfaAffx.16270.1.S1_at | −1.3 | fish oil |
| 12-lipooxygenase | CfaAffx.25908.1.S1_s_at | −1.3 | fish oil |
| MMP2 | CfaAffx.14851.1.S1_s_at | −1.3 | fish oil |
| MMP7 | CfaAffx.23201.1.S1_at | −1.3 | fish oil |
| Transforming growth factor beta receptor 1 | Cfa.13340.1.A1_at | 1.3 | fish oil |
| Facilitated glucose transporter 9 | Cfa.7132.1.A1_at | 1.4 | fish oil |
| Related to energy metabolism | | | |
| PDK4 | Cfa.2282.1.S1_at Cfa.19125.2.S1_at, | 1.4 | control |
| Hexokinase 3 | CfaAffx.25391.1.S1_s_at | 1.3 | control |
| 5' AMP alpha 1 | Cfa.9738.1.S1_s_at | 1.3 | control |
| 5' AMP beta 1 | CfaAffx.15678.1.S1_at | 1.3 | control |
| 5' AMP gamma 2 | Cfa.10276.2.S1_a_at, | 1.4 | control |
| Facilitated glucose transporter 1 | CfaAffx.4630.1.S1_s_at | 1.3 | control |
| Facilitated glucose transporter 6 | Cfa.6832.1.A1_at | 1.3 | control |
| Succinyl CoA ligase alpha | Cfa.16185.1.S1_at | 1.3 | control |
| PPAR gamma | CfaAffx.8402.1.S1_at | 1.3 | control |
| Fatty acid desaturase 1 | CfaAffx.24518.1.S1_at | 1.9 | control |
| cAMP responsice element modulator | Cfa.855.1.S1_at | 1.3 | fish oil |
| PDK4 | Cfa.2282.1.S1_at Cfa.19125.2.S1_at, | 1.6 | fish oil |
| Hexokinase 3 | CfaAffx.25391.1.S1_s_at | 1.3 | fish oil |
| 5' AMP alpha 1 | Cfa.9738.1.S1_s_at | 1.3 | fish oil |
| 5' AMP beta 1 | CfaAffx.15678.1.S1_at | 1.3 | fish oil |
| 5' AMP gamma 2 | Cfa.10276.2.S1_a_at, | 1.5 | fish oil |
| Facilitated glucose transporter 1 | CfaAffx.4630.1.S1_s_at | 1.3 | fish oil |
| Facilitated glucose transporter 6 | Cfa.6832.1.A1_at | 1.4 | fish oil |
| Succinyl CoA ligase alpha | Cfa.16185.1.S1_at | 1.3 | fish oil |
| Succinyl CoA ligase beta | Cfa.1485.1.S1_at | 1.3 | fish oil |
| PPAR gamma | CfaAffx.8402.1.S1_at | 1.3 | fish oil |
| SREBP-1 | Cfa.189.2.S1_s_at | −1.3 | fish oil |

Table 5 illustrates the ingredients in an illustrative pet food composition of the invention.

TABLE 5

Ingredients used to make composition

| | Ingredients |
|---|---|
| 1 | Wheat |
| 2 | Milo |
| 3 | Corn |
| 4 | Ground Chicken |
| 5 | Corn Gluten Meal |
| 6 | Poultry Meal |
| 7 | Soy bean oil |
| 8 | Flaxseed |
| 9 | Rice Brewers |
| 10 | Soybean meal, 49% |
| 11 | Pal enhancer 1 |
| 12 | Beet pulp |
| 13 | Potassium Citrate |
| 14 | Fish oil |
| 15 | DL-methionine |
| 16 | L-lysine HCl |
| 17 | Salt |
| 18 | Calcium carbonate |
| 19 | Lipoic acid |
| 20 | Choline chloride |
| 21 | Vitamin premix |
| 22 | L-threonine |
| 23 | Vitamin E |
| 24 | L-tryptophan |
| 25 | Lipoic acid |
| 26 | Mineral premix |
| 27 | Preservative |

Table 6 illustrates arthritic makers measured in blood samples for dogs after being fed a control diet compared with dogs fed a pet food including lipoic acid for 90 days. As illustrated in Table 5, dogs fed a control plus lipoic acid displayed decreased immune status markers after 90 days.

TABLE 6

Arthritic markers measured in the blood in dogs at day 90 fed different foods[a,b]

| | | | | | Probability, P< | | |
|---|---|---|---|---|---|---|---|
| Metabolite | Control | Upgrade | Upgrade + lipoic | SE | Upgrade vs Control | Upgrade vs +lipoic | control vs +lipoic |
| CPII, ng/mL | 941.1 | 897.8 | 848.0 | 33.56 | 0.18 | 0.15 | 0.01 |
| COMP, U/L | 1.77 | 1.96 | 1.86 | 0.088 | 0.04 | 0.28 | 0.30 |
| CPII:COMP ratio | 535.3 | 460.4 | 483.3 | 41.78 | 0.08 | 0.59 | 0.22 |
| Change CPII | −118.70 | −131.00 | −232.70 | 36.546 | 0.74 | 0.01 | 0.01 |

TABLE 6-continued

Arthritic markers measured in the blood in dogs at day 90 fed different foods[a][b]

| Metabolite | Control | Upgrade | Upgrade + lipoic | SE | Probability, P< | | |
|---|---|---|---|---|---|---|---|
| | | | | | Upgrade vs Control | Upgrade vs +lipoic | control vs +lipoic |
| Change COMP | −1.53 | −1.31 | −1.39 | 0.153 | 0.17 | 0.60 | 0.39 |
| Eicosapentaenoic Acid, mg/dL | 0.15 | 9.88 | 10.4 | 1.259 | 0.01 | 0.69 | 0.01 |

[a]Individual markers analyzed with d 0 as covariate
[b]Change in individual markers and ratios analyzed without covariates.
Control refers to standard AAFCO dog food.
Upgrade refers to a low fat, reduced calorie, high fiber pet food.

Table 7 illustrates arthritic makers measured in blood samples for dogs after being fed five different foods for 180 days.

TABLE 7

Arthritic markers measured in the blood in does at day 180 fed five different foods*

| Metabolite | #1 | #2 | #3 | #4 | #5 | SE | Probability, P< | | | |
|---|---|---|---|---|---|---|---|---|---|---|
| | | | | | | | vs #1 | vs #2 | Vs #4 | vs #5 |
| Osteocalcin, ng/mL | 6.81 | 8.64 | 9.53c | 8.29 | 6.71 | 0.883 | 0.05 | NS | NS | 0.05 |
| Cartilage Oligomeric Matrix Protein, U/L | 3.17 | 3.30 | 3.23 | 3.19 | 3.38 | 0.204 | NS | NS | NS | NS |
| Amino Terminal Crosslink Telopeptide, nM BCE | 21.42 | 25.53 | 24.89 | 24.02 | 23.63 | 2.707 | NS | NS | NS | NS |
| Eicosapentaenoic Acid, mg/dL | 1.88b | 0.49a | 8.07c | 1.79b | 0.47 | 0.388 | 0.05 | 0.05 | 0.05 | 0.05 |

*Day 0 used as a covariate

Table 8 illustrates blood cytokine levels at day 180 to determine treatment effect with initial covariate for dogs fed five different pet foods for 180 days.

TABLE 8

Canine blood cytokine levels at d 180 with d 0 as covariate

| Measure | #1 | #2 | #3 | #4 | #5 | SE | Probability, P< | | | |
|---|---|---|---|---|---|---|---|---|---|---|
| | | | | | | | vs #1 | vs #2 | Vs #4 | vs #5 |
| IL-2 (pg/ml) | 635.2 | 251.60 | 263.9 | 371.00 | 257.10 | 394.21 | 0.20 | 0.97 | 0.98 | 0.77 |
| IL-6 (pg/ml) | 103.7 | 66.8 | 45.9 | 41.7 | 66.50 | 48.606 | 0.11 | 0.55 | 0.55 | 0.93 |
| IL-7 (pg/ml) | 369.0 | 235.9 | 215.7 | 661.6 | 210.4 | 200.49 | 0.30 | 0.89 | 0.97 | 0.02 |
| IL-8 (pg/ml) | 989.8 | 885.0 | 1024.3 | 1261.1 | 833.3 | 227.10 | 0.82 | 0.37 | 0.21 | 0.24 |
| IL-15 (pg/ml) | 477.8 | 390.8 | 280.5 | 476.0 | 374.7 | 247.07 | 0.28 | 0.53 | 0.59 | 0.39 |
| IL-18 (pg/ml) | 458.7 | 200.6 | 172.4 | 297.5 | 262.5 | 238.53 | 0.10 | 0.87 | 0.60 | 0.57 |
| KC (pg/ml) | 803.6 | 643.6 | 653.9 | 592.6 | 589.0 | 105.65 | 0.05 | 0.89 | 0.38 | 0.54 |
| MCP-1 (pg/ml) | 349.2 | 216.8 | 215.4 | 223.7 | 256.2 | 108.13 | 0.09 | 0.99 | 0.60 | 0.93 |
| IP-10 (pg/ml) | 6.05 | 7.93 | 3.98 | 7.76 | 2.89 | 3.572 | 0.41 | 0.12 | 0.68 | 0.25 |
| IFN-gamma (pg/ml) | 31.88 | 29.61 | 15.07 | 9.03 | 19.79 | 25.207 | 0.36 | 0.42 | 0.79 | 0.80 |
| GM-CSF (pg/ml) | 620.9 | 217.2 | 223.7 | 351.8 | 284.2 | 301.51 | 0.08 | 0.98 | 0.78 | 0.65 |

TABLE 8-continued

Canine blood cytokine levels at d 180 with d 0 as covariate

| Measure | #1 | #2 | #3 | #4 | #5 | SE | Probability, P< | | | |
| --- | --- | --- | --- | --- | --- | --- | --- | --- | --- | --- |
| | | | | | | | vs #1 | vs #2 | Vs #4 | vs #5 |
| Total Pro-inflammatory cytokines | 5351.1 | 2394.10 | 2832.2 | 4535.5 | 3284.1 | 1482.30 | 0.02 | 0.70 | 0.68 | 0.22 |

The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

What is claimed is:

1. A method for treating osteoarthritis in a companion animal in need thereof, which comprises feeding the companion animal a composition comprising lipoic acid or a salt thereof in an amount effective to treat osteoarthritis, wherein the effective amount is at least about 25 ppm to 600 ppm.

2. The method of claim 1, wherein the effective amount is at least about 50 ppm.

3. The method of claim 1, wherein the effective amount is at least about 100 ppm.

4. The method of claim 1, wherein the effective is amount is at least about 200 ppm.

5. The method of claim 1, wherein the companion animal is a dog.

6. The method of claim 1, wherein the companion animal is a cat.

7. The method of claim 1, wherein the pet food composition comprising lipoic acid is administered at least 15 days.

8. The method of claim 1, wherein the pet food composition comprising lipoic acid is administered at least 30 days.

9. The method of claim 1, wherein the pet food composition comprising lipoic acid is administered at least 45 days.

10. The method of claim 1, wherein the pet food composition comprising lipoic acid is administered daily.

11. A method for treating a degenerative joint condition in a companion animal in need thereof, which comprises feeding the companion animal a composition comprising lipoic acid or a salt thereof in an amount effective to treat the degenerative joint condition wherein the effective amount is at least about 25 ppm to 600 ppm.

12. The method of claim 11, wherein the amount is at least about 25 ppm.

13. The method of claim 11, wherein the effective amount is at least about 50 ppm.

14. The method of claim 11, wherein the effective amount is at least about 100 ppm.

15. The method of claim 11, wherein the effective amount is about at least about 200 ppm.

16. The method of claim 11, wherein the companion animal is a dog.

17. The method of claim 11, wherein the companion animal is a cat.

18. The method of claim 11, wherein the pet food composition comprising lipoic acid is administered at least 15 days.

19. The method of claim 11, wherein the pet food composition comprising lipoic acid is administered at least 30 days.

20. The method of claim 11, wherein the pet food composition comprising lipoic acid is administered at least 45 days.

21. The method of claim 11, wherein the pet food composition comprising lipoic acid is administered daily.

22. The method of claim 11, wherein the degenerative joint condition comprises osteoarthritis.

23. The method of claim 11, wherein the degenerative joint condition comprises cartilage damage.

* * * * *